(12) United States Patent
Luu et al.

(10) Patent No.: US 7,888,395 B2
(45) Date of Patent: Feb. 15, 2011

(54) STAT3 PHOSPHORYLATION INHIBITOR AND NOTCH1 EXPRESSION INHIBITOR

(75) Inventors: Bang Luu, rue Blaise Pascal (FR); Ellane Mohier, rue Blaise Pascal (FR); Masashi Yamada, Tokyo (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 944 days.

(21) Appl. No.: 11/665,375

(22) PCT Filed: Oct. 13, 2005

(86) PCT No.: PCT/JP2005/018882
§ 371 (c)(1),
(2), (4) Date: Apr. 13, 2007

(87) PCT Pub. No.: WO2006/041135
PCT Pub. Date: Apr. 20, 2006

(65) Prior Publication Data
US 2010/0094061 A1    Apr. 15, 2010

(30) Foreign Application Priority Data
Oct. 13, 2004    (JP)    ............. P. 2004-299415

(51) Int. Cl.
*A61K 31/12*    (2006.01)
(52) U.S. Cl. .................................... 514/690
(58) Field of Classification Search ............. 568/377; 514/690
See application file for complete search history.

(56) References Cited

U.S. PATENT DOCUMENTS

| 4,169,103 | A | 9/1979 | Haenni et al. | |
|---|---|---|---|---|
| 6,552,009 | B2 * | 4/2003 | Achkar | 514/168 |
| 2001/0049365 | A1 | 12/2001 | Achkar | |

FOREIGN PATENT DOCUMENTS

| JP | 2000297034 | 10/2000 |
|---|---|---|
| JP | 2001515058 | 9/2001 |
| JP | 200268973 | 3/2002 |
| WO | 96/21438 A1 | 7/1996 |
| WO | 99/08987 A1 | 2/1999 |

OTHER PUBLICATIONS

Artavanis-Tsakonas, S., et al., "Notch Signaling: Cell Fate Control and Signal Integration in Development," Science, vol. 284, pp. 770-776 (Apr. 30, 1999).
Zlobin, A., et al., "Toward the Rational Design of Cell Fate Modifiers: Notch Signaling as a Target for Novel Biopharmaceuticals," Current Pharm. Biotech., vol. 1, No. 1, pp. 83-106, (Jul. 1, 2000).
Nickoloff, B.J., et al., "Notch signaling as a therapeutic target in cancer: a new approach to the development of cell fate modifying agents," Oncogene, 22 (42), pp. 6598-6608 (2003).
Gonzalez De Aguilar, JL., et al., "Neurotrophic activity of 2,4,4-trimethyl-3-(15-hydroxypentadecyl)-2-cyclohexen-1-one in cultured central nervous system neurons," Brain Research 920 pp. 65-73 (2001).
Bromberg, J., et al., "The role of STATs in transcriptional control and their impact on cellular function," Oncogene 19, pp. 2468-2473 (2000).
Grandbarbe, L., et al., "Delta-Notch signaling controls the generation of neurons/glia from neural stem cells in a stepwise process," Development 130, pp. 1391-1402 (2003).
Tropepe, V., et al., "Distinct Neural Stem Cells Proliferate in Response to EGF and FGF in the Developing Mouse Telencephalon," Development Biology, 208, pp. 166-188 (1999).
Reynolds, B.A., et al., "Generation of Neurons and Astrocytes from Isolated Cells of the Adult Mammalian Central Nervous System," Science, vol. 255, pp. 1707-1770 (1992).
Weijzen, S., et al., "Activation of Notch-1 signaling maintains the neoplastic phenotype in human Ras-transformed cells," Nature Medicine, vol. 8, No. 9, pp. 979-986 (Sep. 2002).

* cited by examiner

*Primary Examiner*—Sikarl A Witherspoon
(74) *Attorney, Agent, or Firm*—Sughrue Mion, PLLC

(57) ABSTRACT

The present invention relates to an agent for suppressing STAT3 phosphorylation and for suppressing Notch1 expression comprising as an active ingredient a compound represented by the following formula (1):

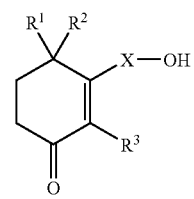

wherein $R^1$, $R^2$ and $R^3$ each independently represents a hydrogen atom or a methyl group; and
X represents a linear or branched alkyl, alkylene or alkenylene group having 10 to 28 carbon atoms.

2 Claims, 3 Drawing Sheets

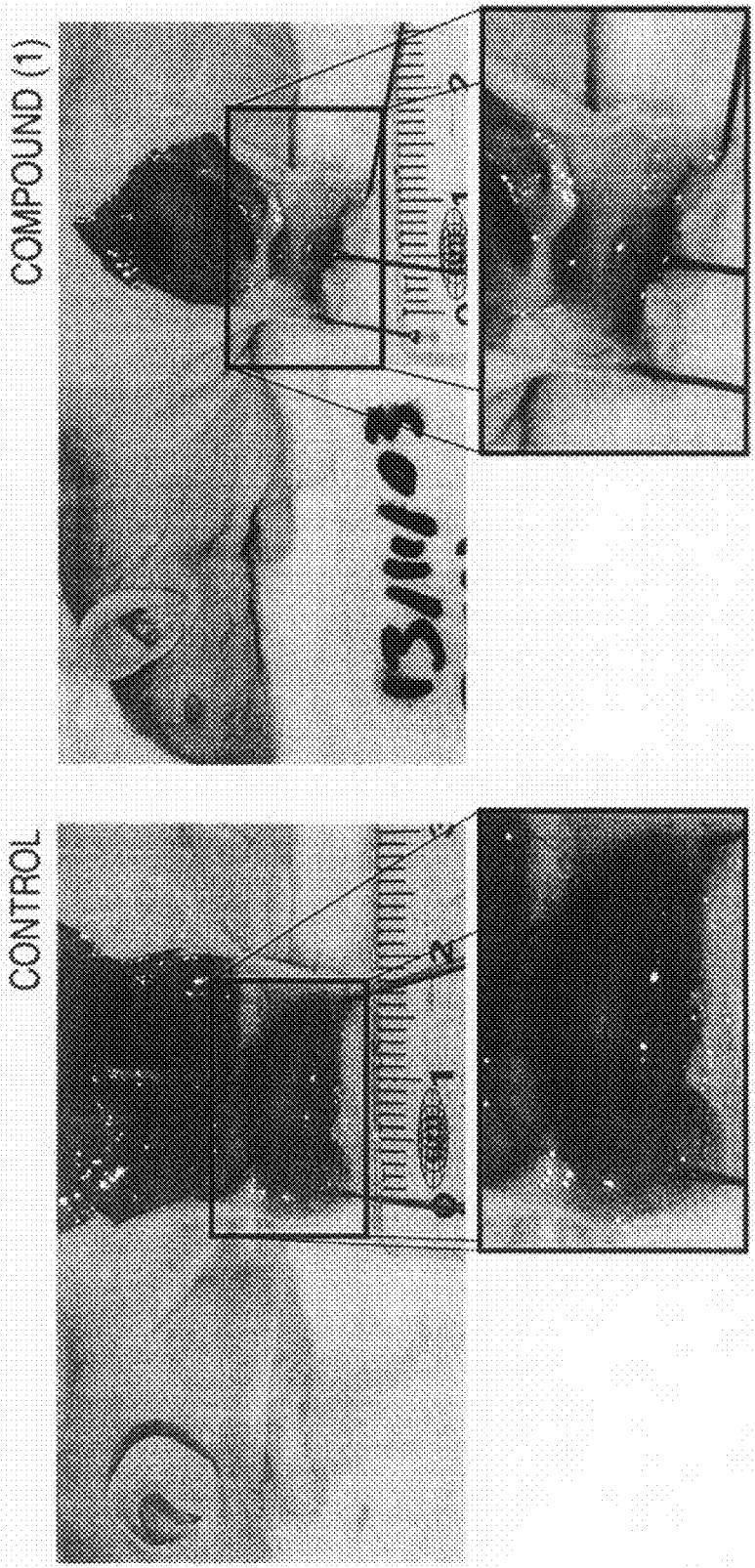

```
                           SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: Synthetic construct

<400> SEQUENCE: 1
tgccaaatgc ctgccagaat                                                 20

<210> SEQ ID NO 2
<211> LENGTH: 20
<212> TYPE: DNA
<213> ORGANISM: Artificial
<220> FEATURE:
<223> OTHER INFORMATION: Synthetic construct

<400> SEQUENCE: 2
catggatctt gtccatgcag                                                 20

<210> SEQ ID NO 3
<211> LENGTH: 25
<212> TYPE: DNA
<213> ORGANISM: Artificial
<220> FEATURE:
<223> OTHER INFORMATION: Synthetic construct

<400> SEQUENCE: 3
gaggcgactc ttctgctgtt gaaga                                           25

<210> SEQ ID NO 4
<211> LENGTH: 25
<212> TYPE: DNA
<213> ORGANISM: Artificial
<220> FEATURE:
<223> OTHER INFORMATION: Synthetic construct

<400> SEQUENCE: 4
atagagtcac tgagctctcg gacag                                           25

<210> SEQ ID NO 5
<211> LENGTH: 21
<212> TYPE: DNA
<213> ORGANISM: Artificial
```

-continued

```
<220> FEATURE:
<223> OTHER INFORMATION: Synthetic construct

<400> SEQUENCE: 5
acactgggag ttctctgtga g                                      21

<210> SEQ ID NO 6
<211> LENGTH: 21
<212> TYPE: DNA
<213> ORGANISM: Artificial
<220> FEATURE:
<223> OTHER INFORMATION: Synthetic construct

<400> SEQUENCE: 6
gctgtctgct ggcatgggat a                                      21

<210> SEQ ID NO 7
<211> LENGTH: 20
<212> TYPE: DNA
<213> ORGANISM: Artificial
<220> FEATURE:
<223> OTHER INFORMATION: Synthetic construct

<400> SEQUENCE: 7
cttctcgtcc tccagctcat                                        20

<210> SEQ ID NO 8
<211> LENGTH: 20
<212> TYPE: DNA
<213> ORGANISM: Artificial
<220> FEATURE:
<223> OTHER INFORMATION: Synthetic construct

<400> SEQUENCE: 8
gctgacatca ggggtgtcac                                        20
```

STAT3 PHOSPHORYLATION INHIBITOR AND NOTCH1 EXPRESSION INHIBITOR

This is a national stage application under 35 U.S.C. §371 of PCT/JP2005/018882 filed on Oct. 13, 2005, which claims priority from Japanese patent application 2004-299415 filed on Oct. 13, 2004, all of which are incorporated herein by reference.

TECHNICAL FIELD

The present invention relates to a non-peptide compound having a low molecular weight acting as a factor of determining cell fate. The compound acts on transduction system via STAT signal and Notch signal by reducing phosphorylation of STAT3 and suppressing expression of a Notch1 receptor. As a result, the compound acts as a differentiation-inducing agent of undifferentiated cells (stem cells). Based on these characteristics, the compound is useful as a preventive or therapeutic agent for clinical conditions induced by dysfunction of both STAT signal and Notch signal transduction systems.

BACKGROUND ART

Notch signal transduction relates to determination of cell fate in youth and adulthood and is a mechanism which is not so changed (Non-Patent Document 1). The Notch signal transduction participates in the determination of cell fate in many tissues. The function of Notch acts on neighboring cells having the same function.

In many cases, it inhibits differentiation toward initial differentiation fate. Instead, it differentiates a cell into second alternative fate or retains the cell in an undifferentiated state. This function is an origin of cell diversity. Other than this role, Notch signal actively promotes differentiation of various types of cells. For example, Notch signal promotes differentiation into astrocytes in a nerve system.

Molecularly, Notch signal was confirmed first in drosophila and then in vertebrates. This depends on a transmembrane receptor encoded by a Notch gene (Non-Patent Documents 1 to 3) and it is activated by a transmembrane ligand (encoded by a gene such as Delta or Jagged). This activation regulates a series of degradation and cleavage of Notch protein and transcription of a fragment which is present in a molecule into a nucleus, which binds to CBF protein. They also act as transcription complexes which activate transcription of HES gene. Since HES inhibits transcription of MASH1 which is a proneuron gene, differentiation of the nerve stem cells into neurocytes is inhibited by activation of Notch in the cells.

By the multifunction thereof, dysfunction of the Notch signal transduction invites various diseases such as tumors, cancers, and neurodegenerative diseases such as Alzheimer's disease (Non-Patent Documents 2 to 3). A cell fate-determining factor acting on Notch signal transduction system becomes a target for novel pharmaceuticals. Since the strategies which have been employed aim at control of Notch function through targeting a factor which exists in downstream of Notch signal system (e.g., suppression of binding of a ligand, inhibition of protein degradation and cleavage of a receptor, suppression of transcription thereof to a nucleus, etc.), they do not suppress expression of Notch.

Non-Patent Document 1: S. Artavanis-Tsakonsa, M. Rand, R. Lake, Notch Signaling: Cell Control and Signal Integration in Development. *Science* Vol. 284 Page 770-776 (1999)

Non-Patent Document 2: A Zlobin, M. Jang, L. Miele, Toward the rational design of cell fate modifiers: Notch signaling as a target for novel biopharmaceuticals. *Current Pharmaceutical Biotechnology* July 1(1) Page 86-106 (2000)

Non-Patent Document 3: B. Nickoloff, B. Osborne, L. Miele Notch signaling as a therapeutic target in cancer: a new approach to the development of cell fate modifying agents. *Oncogene* Vol 22(42) Page 6598-6608 (2003)

The determination of cell fate is an important event in youth as in adulthood. It controls processes such as proliferation, differentiation, and apoptosis of cells. Disorder of such processes is an origin of many clinical conditions.

Therefore, development of a cell fate-determining factor is one of main purposes for the development of pharmaceuticals.

DISCLOSURE OF THE INVENTION

Problems which the Invention is to Solve

An object of the present invention is to provide a compound having a low molecular weight specifically acting on expression of Notch1 gene.

Means for Solving the Problems

It has been already reported that a cyclohexenone long chain alcohol has a neurotrophic activity which promotes living of neurocytes and extension of neurites (Gonzales de Aguilar et al., *Brain Res* (2001) 920, 65-73).

Furthermore, the inventors of the present invention have demonstrated in a test using neurospheres that the compound suppresses differentiation of nerve stem cells into astrocytes and promotes differentiation into neurocytes (PCT: WO 02/29014 A2).

STAT3 is activated by phosphorylation with a large amount of cytokines (growth factors and hormones). Hitherto, 7 kinds of STAT families are specified and some of them can be considerably specifically activated. Biological roles of STAT3 have been clarified by researches with knockout mice and by Cre-LoxP recombination and it is shown that STAT3 plays important roles in various biological functions such as cell proliferation, suppression of apoptosis, and cell motility. On the other hand, activity of STAT3 on ES (embryo stem cells) cells is suppression of self-proliferation of ES cells and promotion of differentiation thereof. Inhibition of STAT3 signal correlates with many cell strains of cancers such as blood cancer, breast cancer, head cancer and neck cancer (Bromberg and Darnell, *Oncogene* (2000) 19, 2468-2473).

As a result of the extensive studies for solving the above problems, the inventors of the present invention have found that a cyclohexenone long chain alcohol has activity of suppressing phosphorylation of STAT3 and activity of suppressing expression of Notch1, and thus have accomplished the present invention.

Namely, the present invention relates to; (1) an agent for suppressing STAT3 phosphorylation and for suppressing Notch1 expression comprising as an active ingredient a compound represented by the following formula (1):

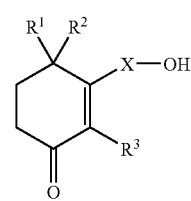

wherein $R^1$, $R^2$ and $R^3$ each independently represents a hydrogen atom or a methyl group; and X represents a linear or branched alkyl, alkylene or alkenylene group having 10 to 28 carbon atoms;

(2) an antitumor agent comprising the above compound (1) as an active ingredient; and (3) an agent for improving STAT signal and Notch signal transduction system dysfunction comprising the above compound (1) as an active ingredient.

Effect of the Inventon

The compound represented by the formula (1) exhibits excellent suppressing effect of STAT3 phosphorylation and suppressing effect of Notch1 expression and is useful as an agent for improving STAT signal and Notch signal transduction system dysfunction. Moreover, since it is revealed that STAT signal and Notch signal transduction system dysfunction causes diseases such as various tumors, cancers, and neurodegenerative diseases such as Alzheimer's disease, the compound represented by the formula (1) is also useful as a preventive or therapeutic agent for various tumors and cancers and various neurodegenerative diseases.

BRIEF DESCRIPTION OF THE DRAWINGS

FIG. 4 is a drawing which shows test results indicating ex vivo antitumor activity of the cyclohexenone long-chain alcohol of the present invention.

BEST MODE FOR CARRYING OUT THE INVENTION

Figure 1:
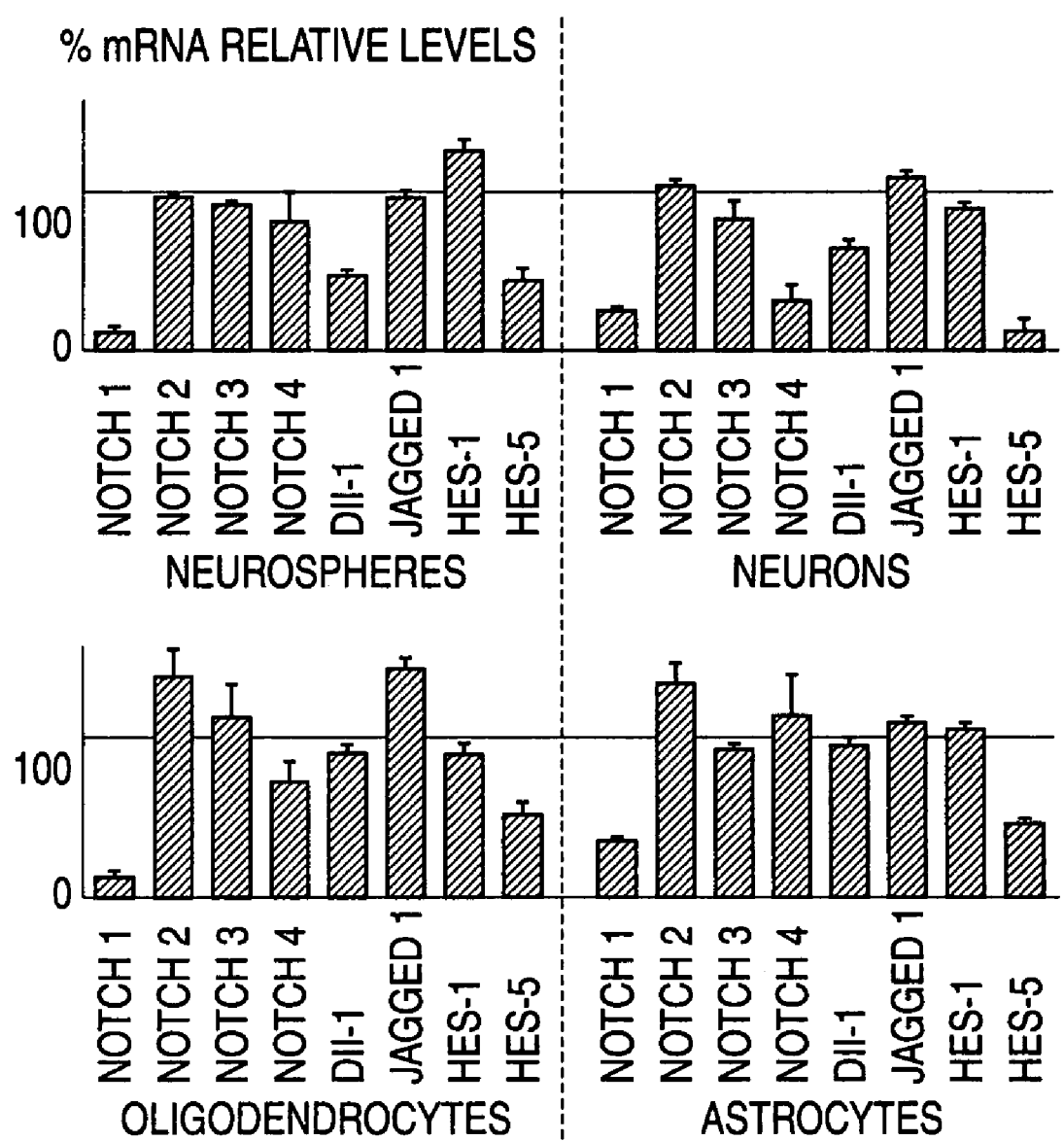
FIG. 1 is a drawing which shows increase or decrease of gene expression depending on presence of addition of the cyclohexenone long chain alcohol of the present invention.

In the above formula (1), X is a linear or branched alkyl, alkylene or alkenylene group having 10 to 28 carbon atoms and an alkyl group having 1 to 10 carbon atoms is mentioned as a side chain in the case of the branched alkylene or alkenylene group. Examples of the side chain alkyl group include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, an isohexyl group, a heptyl group, an octyl group, a nonyl group, a decyl group, and the like. Among these, a methyl group is preferred. Moreover, substitution of the side chain on the linear alkylene group or alkenylene group (which means an alkene structure having at least one carbon-carbon double bond) is preferably carried out in 3- and/or 7-position. Among these X, a linear alkyl group having 10 to 28 carbon atoms is more preferred and a linear alkyl group having 10 to 18 carbon atoms is particularly preferred. Furthermore, $R^1$, $R^2$ and $R^3$ each represents a hydrogen atom or a methyl group, and the case where at least one of them is a methyl group is more preferred.

Additionally, the compound represented by the formula (1) may be in the form of a pharmaceutically acceptable salt, a solvate or a hydrate thereof. As the compound represented by the formula (1), various isomers may be present and these isomers are also included in the present invention.

The compound represented by the formula (1) can be prepared by any known methods and, for example, it can be produced in accordance with the production method described in JP-A-2000-297034.

The compound represented by the formula (1) can be administered either by oral administration or by parenteral (intramuscular, subcutaneous, intravenous, suppository, or the like) administration.

In the case of oral preparations, they can be formulated into tablets, coated tablets, granules, capsules, solutions, syrups, elixirs, oil or aqueous suspensions in a conventional manner after addition of an excipient and, if necessary, a binder, a disintegrator, a lubricant, a colorant, a corrigent and the like. Examples of the excipient include lactose, corn starch, sucrose, glucose, sorbitol, crystalline cellulose and the like. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch, polyvinyl pyrrolidone and the like.

Examples of the disintegrator include starch, agar, gelatin powder, crystalline cellulose, calcium carbonate, sodium bicarbonate, calcium citrate, dextran, pectin and the like. Examples of the lubricant include magnesium stearate, talc, polyethylene glycol, silica, hardened vegetable oil and the like. As the colorant, those which are pharmaceutically acceptable as an additive for pharmaceuticals can be used. Examples of the corrigent include cocoa powder, menthol, aromatic acid, peppermint oil, camphol, cinnamon powder and the like. These tablets and granules may be coated with sugar, gelatin or the like, if necessary.

As examples of parenteral administration, in the case of preparing injections, subcutaneous, intramuscular or intravenous injections are formulated in a conventional manner by adding a pH regulator, a buffer, a stabilizer and/or a preservative, if necessary. The injection may be formulated into a preparation for reconstitution immediately before use as a solid preparation by placing the injection solution in a vial, subsequently lyophilizing the solution and the like. One dose may be placed in a vial or alternatively, multiple doses may be placed in one vial.

In the case of human, the dose of the compound of the present invention as a medicament per adult is usually in the range of from 0.01 to 1000 mg/day, preferably in the range of from 0.1 to 500 mg/day, and the daily dose is administered once a day or may be divided into 2 to 4 portions.

EXAMPLES

Although the following will explain the present invention with reference to Examples, the invention is not limited to these Examples.

Example 1

Gene Expression Test

Treatment with 2,4,4-trimethyl-3-(15-hydroxypentadecyl)-2-cyclohexen-1-one

In ethanol, 2,4,4-trimethyl-3-(15-hydroxypentadecyl)-2-cyclohexen-1-one synthesized by the method described in JP-A-2000-297034 was dissolved to give a concentration of $10^{-2}$ M. The solution was added to a culture solution in a desirable concentration to be final dilution of 1 µl/ml. At different times and different periods in cell culture, 2,4,4-trimethyl-3-(15-hydroxypentadecyl)-2-cyclohexen-1-one was added. As a control, 1 µl/ml ethanol was used (in the diluted concentration, ethanol does not affect on differentiation of the culture solution at all). Each experiment was repeated at least three times.

Formation, Maintenance and Differentiation of Neurospheres

Protocol was adapted from Grandbarbe et al., *Development* (2003) 130, 1393-1402. When briefly explained, as described in Tropepe et al., *Dev. Biol.* (1999) 208, 166-188, primary neurospheres were prepared from telencephalon of wild-type embryo (E14.5) and were maintained as secondary neurospheres by continuous subculture in a serum-free medium (Reynolds and Weiss, *Science* (1992) 255, 1707-1770) containing 10 ng/ml EGF. After propagation for different times, 50 to 100 neurospheres were inoculated to a polyornithine (Sigma)-coated cover slip in the presence of 2 ng/ml EGF and 0.5% FBS and differentiated.

RT-PCR Analysis

Neurospheres were cultured in a "neurosphere medium" containing 10 ng/ml EGF under various conditions for different times (as described in the text, 3 hours, 12 hours, or 24 hours before RNA extraction). Neurocytes (derived from murine 13-14 days fetal brain), astrocytes (derived from Wistar rat neonatal brain), and oligodendrocytes (derived from Wistar rat neonatal brain) were cultured for 24 hours in the presence of 2,4,4-trimethyl-3-(15-hydroxypentadecyl)-2-cyclohexen-1-one (or ethanol). RNA was purified from cultured cells and transcribed. Three independent RNA samples were prepared for individual experiments. cDNA was synthesized at 37° C. for 1 hour from 3 μg of total RNA for neurospheres, 2 μg thereof for astrocytes and oligodendrocytes, and 1.5 μg thereof for neurocytes with 20 μl of a reaction mixture solution containing 200 U M-MLV transcription enzyme (Invitrogen), 0.5 mM dNTP (QBiogen), 5 mM DTT (Invitrogen), 0.01 μg/μl random hexamer (Invitrogen) and 20 U RnaseOUT (registered trademark) (Invitrogen). One tenth of total cDNA was amplified with 20 μl of a reaction mixture solution containing 1.25 U Taq DNA Polymerase (Invitrogen), 0.5 mM dNTPs (QBiogen) and 0.5 μg of each primer. The conditions for PCR were adjusted for each kind of primers and cells targeted in the study. The primers were designed as follows to fit for both of rat and mouse specimens.

```
Notch1 F:
5'-TGCCAAATGCCTGCCAGAAT-3'        (SEQ ID NO: 1)

Notch1 R:
5'-CATGGATCTTGTCCATGCAG-3'        (SEQ ID NO: 2)

Notch2 F:
5'-GAGGCGACTCTTCTGCTGTTGAAGA-3'   (SEQ ID NO: 3)

Notch2 R:
5'-ATAGAGTCACTGAGCTCTCGGACAG-3'   (SEQ ID NO: 4)

Notch3 F:
5'-ACACTGGGAGTTCTCTGTGAG-3'       (SEQ ID NO: 5)

Notch3 R:
5'-GCTGTCTGCTGGCATGGGATA-3'       (SEQ ID NO: 6)

Notch4 F:
5'-CTTCTCGTCCTCCAGCTCAT-3'        (SEQ ID NO: 7)

Notch4 R:
5'-GCTGACATCAGGGGTGTCAC-3'        (SEQ ID NO: 8)
```

Typical cycle conditions were 94° C. for 30 seconds, 55° C. for 30 seconds, and 72° C. for 30 seconds except for HES-5 whose program was 94° C. for 30 seconds, 63° C. for 30 seconds, and 72° C. for 2 minutes. PCR was repeated twice.

The results are represented by percent in gene expression of cells which was already treated with 2,4,4-trimethyl-3-(15-hydroxypentadecyl)-2-cyclohexen-1-one relative to untreated cells (control conditions adjusted to 100% after normalized toward GAPDH). The relative amount of mRNA was quantitatively determined in accordance with BabyImager analysis and NIHimage 1.36.

As a result of molecular analysis of key gene expression of Notch pathway by RT-PCR, it was found that expression levels of the other Notch receptors (Notch 2 to 4) were not changed by the treatment with 2,4,4-trimethyl-3-(15-hydroxypentadecyl)-2-cyclohexen-1-one, while levels of mRNA of Notch1 and then HES5 were always decreased.

Example 2

After preparation of 2,4,4-trimethyl-3-(15-hydroxypentadecyl)-2-cyclohexen-1-one solution ($10^{-8}$ M), Western Blot was performed using STAT3 and phosphorylated STAT3 antibody (STAT3 antibody derived from rabbit, manufactured by Cell Signaling) to confirm the action of 2,4,4-trimethyl-3-(15-hydroxypentadecyl)-2-cyclohexen-1-one on STAT3 phosphorylation.

Figure 2:
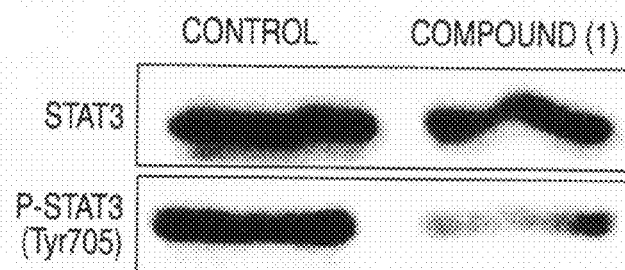
FIG. 2 is a drawing which shows a suppressing activity of STAT3 phosphorylation by addition of the cyclohexenone long chain alcohol of the present invention.

As shown in FIG. 2, the results indicated that the band of a phosphorylated product of STAT3(P-STAT3) was thin in the presence of 2,4,4-trimethyl-3-(15-hydroxypentadecyl)-2-cyclohexen-1-one as compared with the control (the compound was not added). Thus, it was shown that the STAT3 phosphorylation was suppressed.

Example 3

In Vitro Test

Experimental Protocol for 3T3 Ras Transformed Fibroblast

When 3T3 Ras transformed fibroblast was cultured in 10% FBS-containing DMEM medium for 3 days, appearance of "foci" is observed as compared with non-transformed cell strains.

Each of 3T3 Ras transformed fibroblast (derived from mouse) or 3T3 fibroblast (derived from mouse) each is cultured at a concentration of 10,000 cell/ml in 10% FBS-containing DMEM medium for 1 day.

Thereafter, each cell is treated with $10^{-5}$M 2,4,4-trimethyl-3-(15-hydroxypentadecyl)-2-cyclohexen-1-one for 6 days.

Soft Agar Assay

3T3 Ras transformed fibroblast or 3T3 fibroblast is cultured at a concentration of 10,000 cell/ml in 5% FBS-containing DMEM medium which contains 0.625% agar (DIFCO) and $10^{-6}$ M 2,4,4-trimethyl-3-(15-hydroxypentadecyl)-2-cyclohexen-1-one.

Recently, it was shown that the activity of Notch1 is necessary for maintaining neoplastic foci of the cell strain transformed with Ras. Such observation positions Notch signal transduction in a key downstream effecter of tumorigenic Ras and further confirms that Notch may be a novel therapeutic target (Weijzen et al., *Nature Med.* (2002) 8, 979-986).

The fibroblast transformed with Ras was treated with 2,4,4-trimethyl-3-(15-hydroxypentadecyl)-2-cyclohexen-1-one ($10^{-6}$M) and then compared with the untreated cell. Non-transformed cell strains (treated and untreated) were used as controls.

Figure 3:
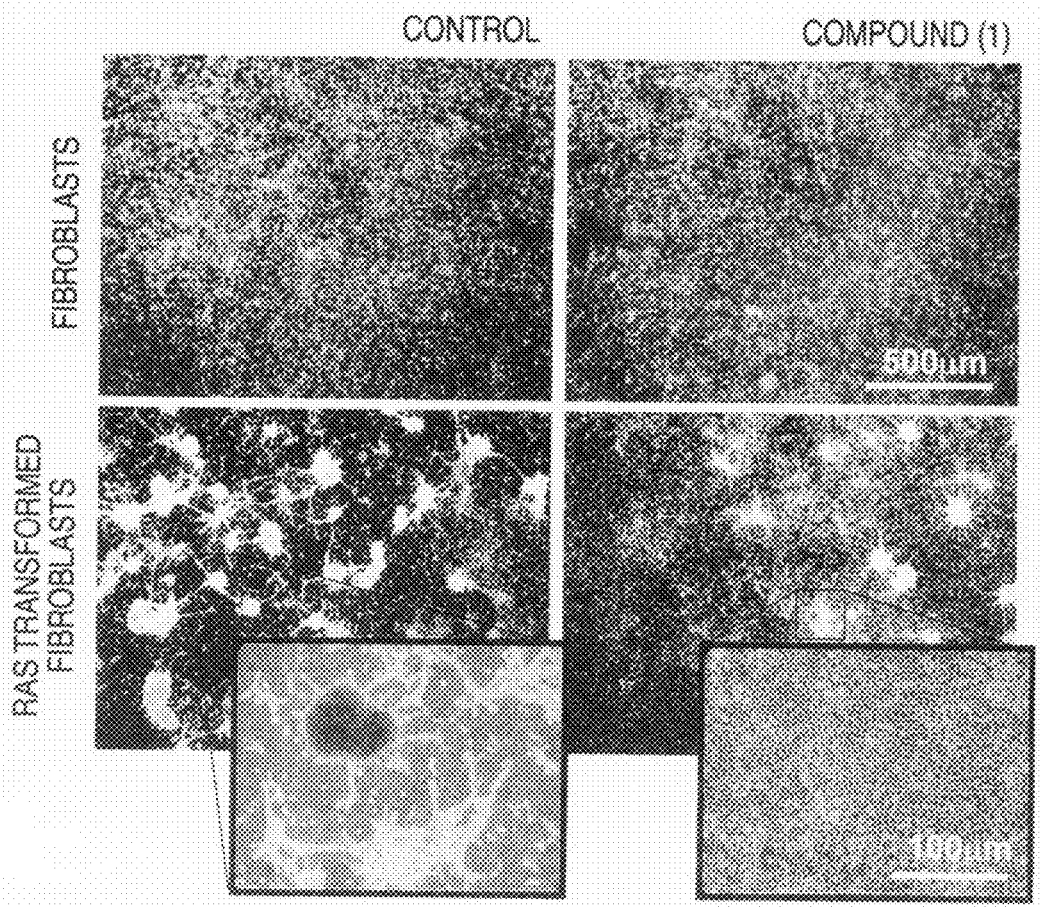
FIG. 3 is a drawing which shows test results indicating in vitro antitumor activity of the cyclohexenone long chain alcohol of the present invention.

From FIG. 3, it was revealed that 2,4,4-trimethyl-3-(15-hydroxypentadecyl)-2-cyclohexen-1-one reduced neoplastic foci of the cell strain transformed with Ras. The finding was accompanied by molecular decrease in Notch1 expression.

Example 4

Ex Vivo Test

In a test tube for 3 days, 3T3 Ras transformed fibroblast (derived from mouse) or 3T3 fibroblast (derived from mouse) was treated with applying 50 μl ($10^{-3}$ M) of 2,4,4-trimethyl-3-(15-hydroxypentadecyl)-2-cyclohexen-1-one. The cell ($2\times10^{-7}$ cells) was again suspended in 400 μl of DMEM medium and 200 μl thereof was injected into 7 weeks-old Swiss Nu/Nu mouse (male) symmetrically. On second, eighth, and fifteenth days after injection, 2,4,4-trimethyl-3-(15-hydroxypentadecyl)-2-cyclohexen-1-one was intraperitoneally administrated into mouse.

From FIG. 4, it was revealed that tumor size was reduced by administration of the cyclohexenone long-chain alcohol.

While the present invention has been described in detail and with reference to specific examples thereof, it will be apparent to one skilled in the art that various changes and modifications can be made therein without departing from the spirit and scope thereof.

The present application is based on Japanese Patent Application No. 2004-299415 filed on Oct. 13, 2004, and the contents are incorporated herein by reference.

INDUSTRIAL APPLICABILITY

The compound represented by the formula (1) exhibits excellent suppressing effect of STAT3 phosphorylation and suppressing effect of Notch1 expression and is useful as an agent for improving STAT signal and Notch signal transduction system dysfunction. Moreover, the compound is useful as a preventive/therapeutic drug for various tumors and cancers and various neurodegenerative diseases.

The invention claimed is:

1. A method for treating cancer comprising administering an effective amount of a composition comprising as an active ingredient a compound which has an activity of improving STAT signal and Notch signal transduction system dysfunction and is represented by the following formula (I):

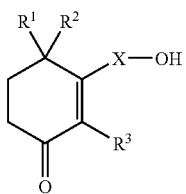

(1)

wherein $R^1$, $R^2$ and $R^3$ each independently represents a hydrogen atom or a methyl group; and
X represents a linear or branched alkyl group,
in a mammal in need of such treatment.

2. A method for treating cancer comprising administering an effective amount of a composition comprising as an active ingredient a compound which has an activity of suppressing STAT3 phosphorylation and suppressing Notch1 expression and is represented by the following formula (1):

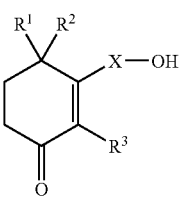

(1)

wherein $R^1$, $R^2$ and $R^3$ each independently represents a hydrogen atom or a methyl group; and
X represents a linear or branched alkyl group,
in a mammal in need of such treatment.

* * * * *